United States Patent [19]
Ludtke et al.

[11] Patent Number: 5,763,186
[45] Date of Patent: Jun. 9, 1998

[54] USE OF ANTISENSE OLIGOMERS IN A PROCESS FOR CONTROLLING CONTAMINATION IN NUCLEIC ACID AMPLIFICATION REACTIONS

[75] Inventors: Douglas N. Ludtke; John E. Monahan, both of Walpole; John T. Unger, Medfield, all of Mass.

[73] Assignee: Chiron Diagnostics Corporation, East Walpole, Mass.

[21] Appl. No.: 778,702

[22] Filed: Jan. 3, 1997

Related U.S. Application Data

[63] Continuation of Ser. No. 157,364, Nov. 23, 1993, abandoned.

[51] Int. Cl.$^6$ .............................. C12Q 1/68; C07H 21/04; C12N 7/00; C12P 19/34
[52] U.S. Cl. .......................... 435/6; 435/91.2; 435/172.3; 435/235.1; 536/24.1
[58] Field of Search ................... 435/91.2, 172.3, 435/235.1, 6; 536/24.1

[56] References Cited

U.S. PATENT DOCUMENTS

| | | | |
|---|---|---|---|
| 4,683,202 | 7/1987 | Mullis | 435/91 |
| 4,786,600 | 11/1988 | Kramer et al. | 435/320.1 |
| 4,987,071 | 1/1991 | Cech et al. | 435/91.31 |
| 5,035,996 | 7/1991 | Hartley | 435/6 |
| 5,112,963 | 5/1992 | Pieles et al. | 536/25.32 |
| 5,221,608 | 6/1993 | Cimino et al. | 435/6 |

FOREIGN PATENT DOCUMENTS

| | | | |
|---|---|---|---|
| 0304184 | 2/1989 | European Pat. Off. | C12Q 1/68 |
| 435380 | 7/1991 | European Pat. Off. | |
| 522884 | 1/1993 | European Pat. Off. | |
| 9207957 | 5/1992 | WIPO | C12Q 1/68 |
| 9325706 | 12/1993 | WIPO | C12Q 1/68 |

OTHER PUBLICATIONS

Miller, P., "Gene Regulation" 1992, Raven Press, NY.
Chu, B.C.F., et al. (1986) Nucleic. Acid Res. 14: (14) 5591–5603.
Coleman, J., et. al., (1985) Nature 315: 601–603.
Cook, P. D., (1991) Anti–Cancer Drug Design 6: 585–607.
Day, A.G. et al. (1991) Proc. Natl. Acad. Sci. USA 88: 6721.
Eguchi, Y. et al. (1991) Annu. Rev. Biochem. 60: 631–652.
Ghosh, M.K. and Cohen, J.S., (1992) Prog. in Nucleic Acid Res. and Molec. Biol. 42: 79–126.
Gray, J., et al., (1992) Plant Molecular Biology 19: 69–87.
Green, et al, (1972) Science 258: 1910.
Han, L. et al (1991) Proc. Natl. Acid Sci USA 88: 4313.
Hjalt, T. et al, (1992) Nucleis Auds. Res. Res. 20: 6723.
Inoue et al, (1987) Nucleis Acid Res. 15: 6131.
Kimura, M. et al, (1992) Manipulation of Myclin Formation in Tranogenic Mice. p. 109 in Murray, J.A.H., Ed., Antisense RNA and DNA, Wiley–Liss, Inc., Pub., 1992.
Lamond I. A and Sproat, B. S., (1993) FEBS Letters 325:(1,2): 123–127.
Lizardi, P.M. et. al., (1988) Biotechnology 6: 1197–1202.
Maher, L. J. et al, (1991) Antisense Research and Development 1: 277–281.
Milligan, J. F., Matteucci, M.D. and Martin, J.C., (1993) J. Medicinal Chemistry 36(14): 1923–1937.
Nielsen P. E., et al (1993) Anti–Cancer Drug Design 8(1): 53–63.

(List continued on next page.)

Primary Examiner—David Guzo
Assistant Examiner—Nancy J. Degen
Attorney, Agent, or Firm—Arthur S. Morgenstern; Helen Greer; Robert P. Blackburn

[57] ABSTRACT

A novel process for the use of antisense oligonucleotides and analogs thereof has been developed. Namely, this technique is useful for the elimination of contamination in the nucleic acid amplification area. Elimination of unwanted contamination has made gene probe analyses much more reproduceable.

22 Claims, 3 Drawing Sheets

OTHER PUBLICATIONS

Nishihara, T., et al (1983) J. Biochem 93: 669–674.
Orum, H. et al (1993) Nucleic Acids Res. 21: 5332.
Rys, P. N. and Persing, D. H., (1993) J. Clinical Microbiol 31(9): 2356–2360.
Schuch, W. (1991) Symp. Soc. Exp. Bio. 45: 117.
To, R.Y, Antisense Control of Retrovirus Replication and Gene Expression, p. 267 in Murray, J.A.H., Ed., Antisense RNA and DNA, Wiley–Liss, Inc., Pub., 1992.

Tuerk, C. et al (1990) Science 249: 505.

Uhlmann, E. & Peyman, A., (1990) Chemical Reviews 90(4): 543–584.

Wolcott, M.J., (1992) Clinical Microbiology Reviews 5(4): 370–386.

Zucker, M. (1989) Methods Enzyme 180: 262.

USE OF ANTISENSE OLIGOMERS IN A PROCESS FOR CONTROLLING CONTAMINATION IN NUCLEIC ACID AMPLIFICATION REACTIONS

This application is a continuation of application Ser. No. 08/157,364, filed Nov. 23, 1993, now abandoned.

BACKGROUND

Nucleic acid amplification methods have been utilized for a number of years as a means of producing adequate quantities of nucleic acids so that laboratories can conduct analyses of these materials. Absent these amplification techniques, these molecules are normally present in samples of tissue or fluids in very minute quantities, often as low as a few molecules. Only some materials are amenable to amplification by culturing techniques, and these require prior knowledge of the material being detected. The culturing techniques also require relatively long periods of time. The nucleic acid amplification techniques, therefore, have become the preferred methods for producing adequate quantities of material for analyses.

A number of amplification techniques have been developed. Polymerase chain reaction (PCR), ligase amplification or chain reaction (LCR), and Qβ replicase (Qβ) are among the techniques widely used. (See Wolcott, 5 Clinical Microbiology Reviews, 370 (1992).) Qβ replicase can be utilized as either a signal amplification system (Chu, B., et al, 1986, Nucleic Acid Research,14(14):5591) or as a target amplification system (Lizardi, P. M., 1988, Biotechnology,6:1197).

One problem with amplification techniques is the frequent occurrence of contamination and the resulting false results from analyses. Contamination of exponential amplification reactions occurs primarily from three sources: cloned target molecules in plasmid vectors that were used for the isolation and characterization of the target sequence; nucleic acids from clinical specimens containing large number of organisms, from cultures used to grow the organism, or from within the reagents used in the amplification reaction (cross-over contamination); or from the products of the amplification reactions themselves (carry-over contamination) (Rys, P. N. and Persing, D. H.; 1993; J. Clinical Microbiol. 31(9):2356–2360). Contamination also occurs as a result of poor "laboratory hygiene".

Since a feature common to exponential amplification methods is that they facilitate the detection of only a few molecules of nucleic acid sequences, the inadvertent presence of even a single molecule capable of being amplified will yield a false positive result. The ability to amplify a single molecule and the ability of a single "contaminating" molecule, from external sources, to be amplified reflects both the power and the major limitation of assays employing exponential amplification. Linear amplification systems will also suffer this limitation if/when their sensitivities are increased to afford the detection of a few molecules.

In this field, contaminating nucleic acid sequences appear as a false positive result. The presence of a "contaminant" in an experiment is recognized by the appearance of a positive result in a negative control. The presence of a "contaminant" in a negative control compromises the validity of the experiment. In some circumstances, a detection method may be available that discriminates between a false positive and a true positive result. With a target specific detection method, an additional risk is that the contaminating sequence will "out compete" the desired template for amplification, the presence of the contaminant would then result in a false negative assay result. In contrast, if the amplification method is used to generate a "signal" then any contaminating sequence which amplifies would result in a false positive assay result.

The ability to determine if any individual experimental result is due to "contamination" can be estimated by the frequency of false positives among the negative controls. Only a limited amount of confidence can be assured if only a single negative control is used, and complete confidence can only be achieved if the entire experiment consists only of negative controls.

Hence contamination control is required for any exponential amplification method capable of amplifying a few molecules of nucleic acid to a detectable limit. The major source of contamination is described as "carry-over" contamination. A series of contamination control measures common to any amplification method can be described as "laboratory hygiene" controls. These include assay protective steps such as dedicated equipment and space, "clean room procedures", spatial segregation of the process steps and physical decontamination or sterilization methods.

A number of other contamination control techniques have been utilized. (1) A containment pack has been developed by Kodak to help prevent contamination. The pack consists of sealed-disposable reaction chambers for the addition of the sample, the amplification of the nucleic acid sequences contained in the second and the detection of amplified products. The reagents required for the amplification reaction and detection would be contained within the pack. The amplification products would presumably never leave the pack eliminating the possibility of carry-over contamination. (See EP Pat. #0435380) (2) Iso-psoralen and related compounds form cyclobutane adducts with pyrimidine bases when added to DNA samples and exposed to longwave UV light. The modification of the pyrimidine bases of both the sample DNA and the amplification products prevents the nucleic acids from being amplified by template-dependent enzymes. (See products developed by HRI Research, Inc. and U.S. Pat. Nos. 5,112,963 and 5,221,608.) (3) Techniques utilizing dUTP or related compounds instead of dTTP in DNA amplification reactions are used to create products which can be differentiated from normal sample DNA. Carry-over contamination caused by amplification products containing uracil can be degraded with the enzyme uracil DNA glycosylase prior to amplification of a sample. (See U.S. Pat. No. 5,035,996.)

Antisense is a concept that has been recently investigated, primarily as a therapeutic tool. Antisense nucleic acids are single-stranded RNA's or DNA's that are complementary to the sequence of their target genes. Base-pairing interactions between the target and the antisense sequences determine their specificity. (Milligan et al, 1993, J. Med. Chem. 36:1923–37; Uhlmann et al, 1990 Chem. Rev. 90:543–84) Several systems which employ the antisense concept also exist in nature. For example, in plasmid replication, RNA interacts with an antisense RNA to yield double stranded RNA which blocks/modulates its replication.

Several therapeutic applications for antisense oligonucleotides have been developed. First, translational blockers, which prevent gene expression by blocking translation of mRNA to protein, may function by inhibiting RNA splicing, by inhibiting transport of mRNA, by changing its secondary structure so that it is not recognized by ribosomes, or by decreasing a specific mRNA half-life, for instance by increasing its sensitivity to ribonucleases. Second, antisense oligonucleotides have been used to block transcription of genes by using them to form a triple-helix structures with the double-stranded DNA. In this context, the antisense oligomer is used as a repressor of gene expression. (See Maher et al. 1 Antisense Research and Development 277, 1991.) Either sequences encoding the control region or the protein coding region of a specific gene can be target sites for triple helix formation. Third, replication of viral genomic RNA to DNA has been shown to be blocked by antisense oligonucleotides complementary to the tRNA primer binding site. Blocking the binding of this primer inhibits DNA polymerization by reverse transcriptase. (R. Y. To, Antisense Control of Retrovirus Replication and Gene Expression, in Antisense RNA and DNA p.267–284 1992 Wiley-Liss Inc. James A. Murray Ed.)

As indicated above, most of the work to date relating to the antisense concept has been applied to therapeutics, primarily in the human area. Another application is their use in basic research to study a gene products function when specific mutations of the gene are not available (Kimura, M. et al.,1992. Manipulation of Myelin Formation in Transgenic Mice, in Antisense RNA and DNA, p. 109–120, Wiley-Liss, Inc. J. A. Murray ed.). An application in botany has been the development of a genetically engineered tomato in which spoilage is retarded. In tomato plants with antisense PG (polygalacturonase) genes inserted into its genome, the production of PG is decreased. The reduction in the amount of PG in the tomato results in a decrease in the degradation of pectin molecules in the cell walls prolonging ripening of the fruit. (Schuch, W., 1991, Symp. Soc. Exp. Biol., 45:117–127.)

Some therapeutic applications have been restricted by the stability of the antisense oligonucleotides. Nuclease degradation of oligodeoxyribonucleotides (natural bases) may dramatically decrease the specificity and/or binding affinity of the oligonucleotide and cause toxic side effects not observed with the full length oligonucleotide. The development of chemically modified nuclease resistant analogs has helped to overcome this problem (Cook, P. D., 1991, Anti-Cancer Drug Design, 6:585–607). The development of modified nucleic acid compounds that bind more strongly to the target nucleic acids than naturally occurring chains increase the stability of the antisense-target hybrid duplex. Work to identify the optimum target sequences for binding antisense oligonucleotides has also been undertaken (Hjalt, T. and E. G. Wagner, 1992, Nucleic Acid Res. 20(24):6723–6732).

SUMMARY OF THE INVENTION

A novel process for the use of antisense oligonucleotides and analogs thereof has been developed. Namely, this technique is useful for the elimination of contamination in the nucleic acid amplification area. Elimination of unwanted contamination has made gene probe analyses much more reproduceable.

DETAILS OF THE INVENTION

Analysis of nucleic acids has the potential of becoming a very useful technique for the determination of the presence of disease. Analyses employing amplification currently suffer from the drawback that contamination is a very serious problem which introduces much uncertainty into gene probe assays. Although the inclusion of controls in all experiments is good laboratory technique, multiple controls must be built into the experimental design of gene probe experiments in order to be able to identify whether contamination has occurred. If contamination is found, it is often difficult, if not impossible, to identify the nature of the contaminant, and even more difficult is the ability to control the contamination. The novel procedure of using antisense compounds as a means of controlling contamination in gene probe experiments has been found to be a successful method of controlling contamination, particularly in the repetitive analyses which are likely to occur in the human diagnostic area, where the type of contaminant may be more easily predicted.

Figure 1:
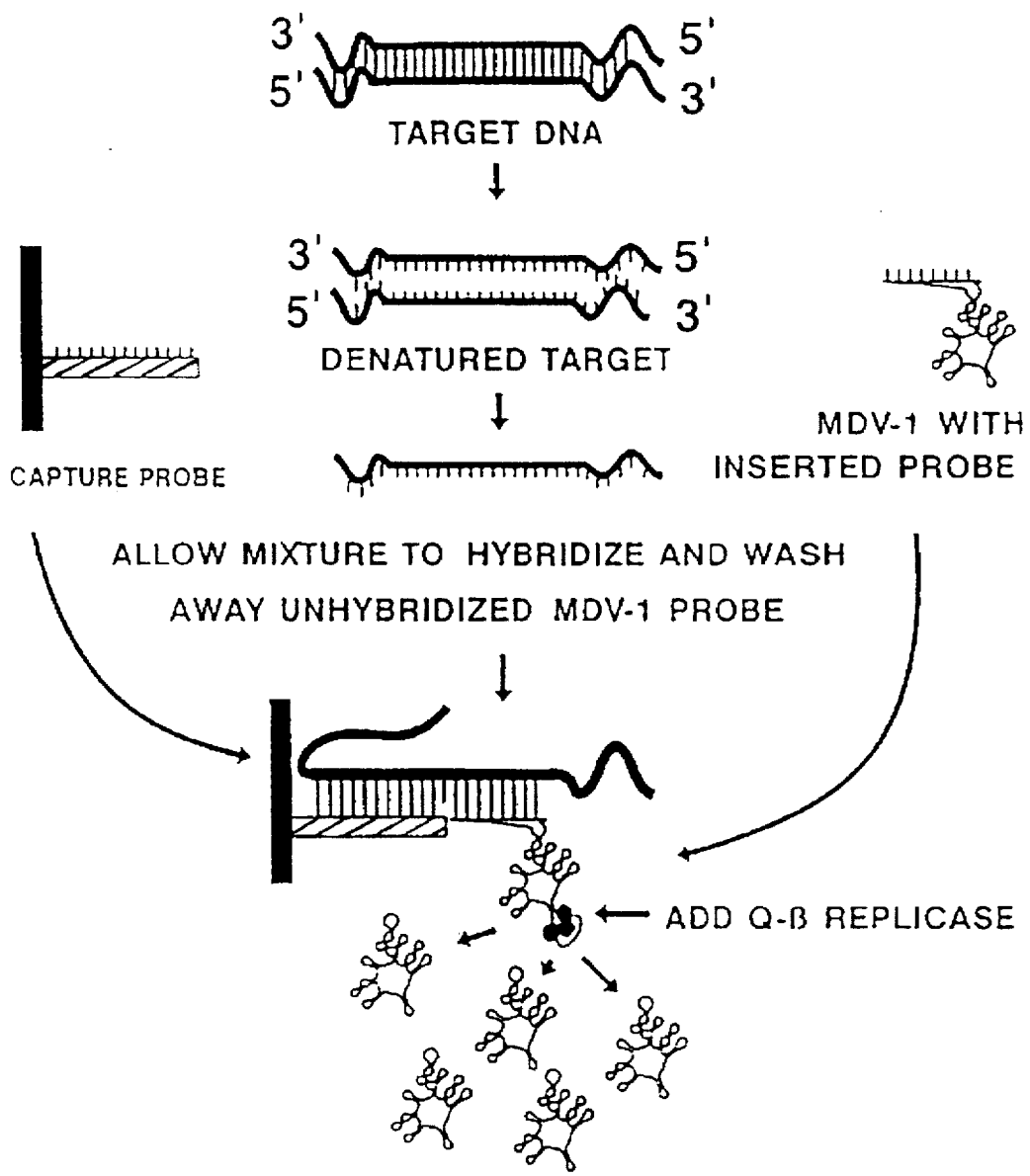
FIG. 1 outlines the mechanism by which a Qβ signal amplification system operates.

While contamination is likely to occur in all the amplification techniques used in the gene probe area, it is particularly true in the Qβ technique. A Q-βReplicase based exponential amplification method was first described as "signal amplification" method (see FIG. 1, from Wolcott, M. J., Clin. Microbiol. Rev. 5:#4 pp370–386 (1992); see also Chu, B. C. F. et. al. Nucl. Acids Res. 14:#14 pp5591–5603 (1986)). Later a target dependant Q-β Replicase based exponential amplification method was also described (Lizardi, P. M., Biotechnology 6:pp1197–1202 (1988).

The design of the Ciba Corning Diagnostic Q-0 Replicase based exponential amplification method is a target dependant system. One reason for this was the ability to perform a target specific detection step which could discriminate the desired product from a contaminant.

Several antisense "clamps" have been developed and evaluated for contamination control. "Clamps" are meant to refer to antisense compounds, that is, nucleic acid oligomers which bind to complementary regions on target nucleic acids and prevent replication of the target nucleic acids. The invention utilizes oligonucleotides with sequences which are complementary to sequences present in the contaminant but not found in the molecules to be amplified. Antisense nucleic acids are single-stranded RNAs or DNAs that are complementary to the sequence of their target genes (Antisense RNA and DNA; J. A. H. Murray, Editor; Willey-Liss Inc. Publisher 1992). Since this is an in vitro technique, the antisense oligonucleotides in this invention target sequences which can be replicated directly without requiring the processes of transcription or translation. Thus, the purpose of the invention is to control contamination by blocking the amplification of contamination molecules without interfering with the amplification of the intended target.

It is known that the pairing of nucleic acids results from the balancing of 2 competing forces. First, the 2 chains repel each other because of the relatively negative charges of the phosphate backbones. Countering these forces is the attraction caused by the bases (hydrogen bonding) and by the stacking of the bases in the helical chains (hydrophobic interactions). These pairs can easily be separated by denaturation, which can be achieved by the application of heat.

A number of factors have been considered in the development of antisense clamps. Knowledge of the nucleic acid sequences of the contaminants and the true target is required to be able to choose clamps which block only the contaminant. Secondary structures formed by the contaminant sequences, length, and melting temperature of the clamps are among those factors. In an exponential amplification, it is also theoretically preferred to block the amplification of the contaminant by using a "clamp" to each of the nucleic acid strands of the contaminant. However, using the technique discussed herein, success was achieved when a clamp to only 1 strand of the contaminant was utilized.

In order to block the amplification of a contaminant nucleic acid, it is first necessary to identify the nucleic acid sequence of both the desired and contaminant nucleic acids. The procedure for determining the sequence of a "clamp" is to select a nucleic acid sequence on the contaminant that is different from that found on the desired nucleic acid. From the sequence information, the secondary structure of the potential target regions can be determined (Zuker, M. 1989, Methods Enzymol. 18:262–288).

Sufficient knowledge has been developed to determine optimum placement of antisense oligonucleotides with respect to the secondary structure of the target regions [Hjalt, T. et al. 1992, Nucleic Acids Research 20(24):6723–6732] For example, a stem-loop formation is a particularly good target. The sequences of one side of the stem, the loop, and a few bases of the opposite stem might be chosen as a target.

Some nucleoside modifications have been found to increase the binding affinity to the RNA complement when the oligonucleotides formed therefrom are used as clamps. For example, O-2-methyl derivatives have been used for this purpose. These monomers have the added benefit of being able to be synthesized into oligomers on a nucleic acid synthesizer. Several types of modified nucleotides or nucleosides have been developed for incorporation into antisense oligonucleotides to increase oligonucleotide or duplex stability [Cook, P. D., 1991, Anti-Cancer Drug Design 6: 585–607; Inoue et al, 1987, Nucleic Acids Res. 15:6131–48; Lamond et al, 1993, FEBS Letters 325:123–7]. Duplex stability can be increased by decreasing the repulsion between the strands of the nucleic acid by reducing the charge on the backbone (for example, using a polypeptide linkage instead of a phosphate linkage; see Nielsen P. E., 1993, Antisense Drug Res. 8(1):56–63). Once the type of oligonucleotide to be used as a "clamp" is chosen, the proper length is determined to fit the thermodynamics of the amplification system.

Antisense expertise developed so far suggests that certain other safeguards be observed. Higher specificity may be required if the target RNA is very long, since this may increase the likelihood that partial base pairing may occur between a "short" base sequence on the antisense oligonucleotide and a complementary sequence on a non-target nucleic acid. Furthermore, much is known about conditions favorable for antisense hybridization reactions: the length of oligomer, the concentration of oligmer, temperature, and cation nature and concentration. It is also preferred that any one clamp not overlap any other by more than 10 bases or 30% of the bases or 3 sequential bases. (See, for example, Ghosh and Cohen, 42 Prog. in Nucleic Acid Res. and Molec. Biol., 79, 1992.)

In vivo applications for antisense have been previously described. Viral resistance in animals, plants and bacteria has been introduced via the use of antisense genes. (See Day, PNAS USA 1991; Han, PNAS USA 1991; Coleman, 1985, Nature 315:601–3.) The antisense technique has in the instant invention found unexpected application in the in vitro area for contamination control. The clamp sequence is chosen, synthesized and added to the analytical sample, which contains both desired and contaminant nucleic acids. When the paired nucleic acids are denatured, the "clamp" anneals to the target (contaminant) nucleic acid and prevents the amplification of this nucleic acid. When the sample is then amplified using one of the amplification schemes, only the desired nucleic acid is amplified.

The term nucleic acid has been generally used in this disclosure, since the techniques discussed herein are applicable to DNA, PNA (peptide-nucleic acid) and RNA molecules. The discussion has also, in general, applied to the case where there is only one contaminant present and one desired nucleic acid. However, the technique is also applicable in situations when there are two or more contaminants present and when there are two or more desired nucleic acids present. The critical factor is that the target nucleic acid sequence in a contaminant not be one which is present in a desired nucleic acid.

Several other precautions should be observed. First, if there are two or more contaminants present, it is important that the target sequences are not complementary to each other. Otherwise, the clamps may bind to each other rather than bind to the targets. Second, if clamps to both strands of a nucleic acid pair are being used, it is important that complementary targets not be used, since, in this case also, the clamps may bind to each other rather than inactivate the contaminants. However, as indicated above, clamps to only one strand of a nucleic acid pair have been found to inactivate that contaminant.

Other techniques may be used to discover "clamps". Two examples of techniques now available would be the screening of large numbers of random oligomers (a combinational library) or through an in vitro "selection" technique such as the "SELEX" (Systematic evolution of ligands by exponential enrichment) method developed by Tuerk & Gold (Tuerk, C., Gold, L., 1990, Science 249: 505). See also Green et al, 1992, Science 258: 1910–5.

It is obvious that an antisense oligomer which has the additional property of being a ribozyme would also be useful in the application of this invention. Ribozymes are RNA enzymes which "can act as endoriboucleases, catalyzing the cleavage of RNA molecules with a sequence specificity of cleavage . . . , thus serving as RNA sequence specific endoribonucleases". (Chech T. R. Zaug, A. J. Been, M. D. U.S. Pat. No. 4,987,071).

There are a number of variations that are application to the above process. First , it is possible to decontaminate the mixture either before or after the amplification step. In the event that decontamination takes place after amplification, complete inactivation of all nucleic acids can be undertaken to prevent carry-over contamination. The decontamination before amplification could apply to merely one or more nucleic acids that are suspected of being sources of contamination. Second, it is possible, if desired, to separate the contaminating nucleic acids from the desired nucleic acids. For example, by attaching the clamp to a solid phase (e.g., a magnetic particle), it would be possible to separate the contaminating nucleic acids. Third, it is possible to link chemical moieties to the antisense nucleic acids such that these chemical moieties can interact with the contaminating nucleic acids (forming, in some cases, covalent chemical bonds), such that the contaminating nucleic acids are inactivated. The invention herein, however, is not limited in its usefulness to merely the exponential amplification techniques identified herein, but also to other amplification techniques (e.g., linear amplification techniques). Furthermore, other variations in the technique described herein will be apparent to those with ordinary skill in the art.

The following examples are intended to illustrate the present invention, but are not intended to limit the scope of the invention. All of the examples utilize a Q-β replicase based exponential amplification. Q-β replicase shows a high specifity for the "+" and "−" viral RNA strands, the natural templates of the enzyme. However it is well documented that Q-β replicase will also bind to small RNA "variants" and replicate them in an exponential manner. One of these families of variants, midivariant (MDV), is approximately 220 nucleotide long RNA. The MDV sequence used in this invention as either RNA or DNA is 220 nucleotides in length and is homologous to the prototype MDV-1 sequence (Nishihura, T., et. al., J. Biochem. 93: pp669–674 (1983)). The MDV molecule is the basis of a series of amplification schemes, wherein the sequence inserted into MDV is amplified. (See, for example, U.S. Pat. No. 4,786,600.) Another of these variants, nanovariant (nV), an approximately 90 nucleotide long RNA has also been widely used. Since these and related molecules are exponentially amplified they can and have become "contaminants" in other assays.

EXAMPLE 1

Experiment to demonstrate the need for additional contamination control procedures:

A set of four amplification experiments were run in a balanced experimental design to examine the performance of the Q-β amplification system with defined templates (synthetic DNA). Both "negatives" (no added template) and a series of templates for Q-β replicase were used. The templates included: MDV-CF DNA (Sequence Number 1), MDV-CA DNA (Sequence Number 2), MDV DNA (Sequence Number 3), nV DNA (Sequence Number 4) and MDV-CA RNA (Sequence Number 5). Note that CA and CF are specific sequences inserted in the MDV chain. Templates were used at either $10^3$ or $10^5$ molecules for the MDV-CF or at $10^5$ molecules for MDV, MDV-CA, or nV. Ten µl of the template mixture was added to 100 µl of a Qβ amplification reaction containing: 2 µg Qβ replicase, 1 mM NTP's (i.e., 1 mM of each of the four nucleotide triphosphates), 100 mM Tris/HCl pH 7.6, 15 mM $MgCl_2$. The amplification mixtures were incubated at 37° C. for 90 minutes, EDTA pH 8.0 was added to a final concentration of 83 mM, and the tubes were placed on ice.

In each of the four experiments the amplification products were analyzed by three methods. First, the CF Target Specific Magic Lite Detection assay was performed to determine if the amplification product contained the insert. Second, the amount of RNA product which was synthesized was measured by an ethidium bromide fluorescence assay. And finally, each sample was analyzed on a denaturing acrylamide gels (with ethidium bromide staining) to determine what product(s) were made.

Results: The combined results of all four experiments using the CF-target specific magic-lite detection assay are shown below. This assay is dependant on "target" amplification since only MDV molecules which have a CF-target will be detected in this sandwich hybridization based detection assay. In the table shown below 288 assay points were collected. In 96 samples, a MDV-CF DNA template had been added, the remaining samples either had no template added or had one of the other templates (described above) added. Only the MDV-CF template has the appropriate target for detection in this assay.

| CF Target Specific Magic-Lite Detection Assay | | | |
|---|---|---|---|
| | MDV-CF Input | | |
| Four Experiments | Positive | Negative | Total |
| Assay Result | | | |
| Positive | 49 | 1 | 50 |
| Negative | 47 | 191 | 238 |
| Total | 96 | 192 | 288 |

The observed sensitivity was only 51% (or 49/96). Sensitivity here is an assessment of the "assay" performance (amplification+detection) with a known positive template (MDV-CF). The specificity was 99.5% (or 191/191). Specifity here is an assessment of the "assay" performance (amplification+detection) in the absence of a known positive template.

The amplification assay shows good specifity but poor sensitivity with a target specific detection assay (a "target amplification" format).

The same samples were also analyzed for the presence of any RNA product (ethidium bromide fluorescence assay). With this detection assay the amplification becomes a "signal amplification" format. With this format the following results were obtained:

| Non-Specific RNA Detection Assay | | | |
|---|---|---|---|
| | Any Template | | |
| Four Experiments | Positive | Negative | Total |
| Assay Result | | | |
| Positive | 189 | 31 | 220 |
| Negative | 10 | 58 | 68 |
| Total | 199 | 89 | 288 |

Since a non-specific RNA detection assay (ethidium bromide fluorescence assay) was used, any sample which had a Qβ replicase template added should be "+" while only the assay "−" controls should yield a "−" assay result. The observed sensitivity was 95.2% while the specifity was 65.0%. The amplification assay shows good sensitivity but poor specificity in the signal amplification format.

The nature of the "false negatives" obtained with the CF target specific magic-lite detection assay and the "false positives" obtained with the non-specific RNA detection assay were addressed by the third detection assay which utilized denaturing PAGE (polyacrylamide gel electrophoresis) with ethidium bromide staining. The denaturing polyacrylamide gels are able to distinguish the replication products based on their apparent size. In two of the four experiments, nanovariant contaminant was observed in both the negative controls and in place of whatever template had been added. The samples which had been templated with MDV-CF were observed to produce only a nanovariant replication product.

Based on the denaturing acrylamide gels described, "clean" and "dirty" amplification were distinguished. A dirty amplification is an amplification which yields an RNA product in the absence of an added template or one or in which an RNA product differs from the added template. In both of the "dirty" runs the contaminant was nanovariant, however nanovariant was not "used" as a template in either of these experiments. Hence the nanovariant contaminant was "environmental" in origin and reflects a carry-over contamination event.

In this circumstance, a detection method was available that could discriminates between a false positive and a true positive result. Based on the denaturing PAGE, the CF-target specific magic-lite detection assay results were separated into the two "clean" amplifications and the two "dirty" amplifications. (See 2 tables below.)

| "Clean Amplifications" | MDV-CF Input | | |
|---|---|---|---|
| | Positive | Negative | Total |
| Assay Result | | | |
| Positive | 46 | 0 | 46 |
| Negative | 2 | 96 | 98 |
| Total | 48 | 96 | 144 |

Sensitivity = 95.8%
Specifity = 100%

| "Dirty Amplifications" | MDV-CF Input | | |
|---|---|---|---|
| | Positive | Negative | Total |
| Assay Result | | | |
| Positive | 3 | 1 | 4 |
| Negative | 45 | 95 | 140 |
| Total | 48 | 96 | 144 |

Sensitivity = 6.2%
Specifity = 99.0%

Conclusions: The AE Detection Assay is Specific (99.5%), but overall the sensitivity with the AE Detection Assay was only 50%.

The low sensitivity ("false negatives") was due to "carry-over" contamination with nano-variant (two "dirty runs" out of four). The sensitivity could be increased too 95.8% by the rejection of the experiments which were contaminated.

In summary, the nature of the problem in the presence of a "contaminant" is dependant on the detection format employed. In the target amplification format a low specifity and a corresponding "false positive" problem is encountered. Hence regardless of the detection format contamination must be controlled.

EXAMPLE 2

Blocking nucleic acid amplification with Nano-44 or Nano-64, antisense oligodeoxyribonucleotides:

Oligonucleotide, Nano-44 (Sequence Number 6) or Nano-64 (Sequence Number 7), complementary to the negative strand of nanovariant RNA (Sequence Number 8), was used to block the replication of nanovariant RNA by Qβ replicase. Either of the oligonucleotides was annealed to the nanovariant template by adding 10 pmoles of oligonucleotide to 25 μl of $H_2O$ containing $2\times10^6$ moles of nanovariant RNA and heating to 70° C. for 10 minutes. A control solution was also made containing only nanovariant RNA. The mixture was allowed to cool at room temperature for 20 minutes.

2.5 μl of the nanovariant RNA/oligonucleotide mixture was added to 50 μl a Qβ amplification reaction containing: 2 μg Qβ replicase, 1 mM NTP's, 100 nmoles $^{32}$P-CTP, 100 mM Tris/HCl pH 7.6, 15 mM $MgCl_2$. Each nanovariant RNA/oligonucleotide mixtures and the nanovariant RNA control solution were used to template four amplification mixtures each. The amplification mixtures were incubated at 37° C. for 90 minutes. EDTA pH 8.0 was added to a final concentration of 83 mM, and the tubes were placed on ice.

Incorporation of NTP's into RNA was detected by DE-81 filter assays. The results are found in Table 1.

| Sample | Nanovariant + Nano-44 | Nanovariant + Nano-64 | Nanovariant |
|---|---|---|---|
| 1 | 3 | 71 | 7737 |
| 2 | 25 | 9140 | 4714 |
| 3 | 4131 | 11907 | 8605 |
| 4 | 31 | 57 | 6634 |
| Average | 1048 | 5293 | 6922 |

The pre-annealing of oligonucleotide Nano-44 decreased the amount of $^{32}$P-CTP incorporated into RNA by 85%, whereas oligonucleotide Nano-64 decreased it by 24%. Because these oligonucleotides are complementary to only the negative strand of nanovariant RNA, linear amplification of the positive strand can occur.

EXAMPLE 3

Investigation into the use of O-2 methyl molecular clamps to inhibit contamination from nanovariant molecules:

Method: Seven O-2 methyl oligomers were synthesized so as to be complementary to either the nanovariant (nV) "−" (Sequence Number 8) or "+" (Sequence Number 9) replication product. The "A" column indicates which of the 4 "−" oligomer clamps (Sequence Numberes 10 to 13) were used, while the "B" column indicates which of the three "+" oligomer clamps (Sequence Numbers 14 to 16) were used. These clamps were synthesized and diluted in DEPC (diethylpyrocarbonate) treated water to 10 uM and stored @ −70°C. The 2× hybridization buffer consisted of 200 mM Tris/HCl pH 7.6, 30 mM $MgCl_2$. The assay components for hybridization were added to sample tubes (all held on ice) as shown below:

| nV ul | repli- cates | clamp combination A (5 ul) | clamp combination B (5 ul) | 2X hybridization buffer ul | Water ul | |
|---|---|---|---|---|---|---|
| 5 | n = 4 | 1 | 5 | 25 | 10 | |
| 5 | ↓ | 1 | 6 | 25 | 10 | |
| 5 | ↓ | 1 | 7 | 25 | 10 | |
| 5 | ↓ | 2 | 6 | 25 | 10 | |
| 5 | ↓ | 2 | 7 | 25 | 10 | |
| 5 | ↓ | 3 | 7 | 25 | 10 | |
| 5 | ↓ | 4 | 5 | 25 | 10 | |
| 5 | ↓ | 4 | 6 | 25 | 10 | |
| 0 | n = 8 | 0 | 0 | 25 | 25 | Negative |
| 5 | n = 8 | 0 | 0 | 25 | 20 | Positive |

The samples were incubate @ 37° C. for 15 min and the hybridization was stopped by cooling on ice. The amplification step was started with the addition of 50 ul of a amplification mix containing Q-Beta Replicase and the required nucleotides. The amplification was carried out @ 37° C. for 90 min and stopped with the addition of 20 ul of 0.5M EDTA. The amount of RNA made was measured by determining the $^{32}$P-CMP incorporated with the DE81 Filter assay and quantified with the Betascope (made by Betagen).

Betascope Detection: Six microliters of each of the stopped reaction mixture were transferred to DE-81 filter paper. The filter was washed in 0.5M sodium phosphate wash buffer (~200 ml), three times, for ten minutes for each wash. After washing the incorporated counts were collected for thirty minutes on the Betascope.

PAGE Analysis: All samples were run out on a 15% polyacrylamide, 40% formamide gels. The samples were loaded in formamide loading dye, boiled for 5 minutes, snap cooled for 2 minutes. The gels were run at 300 volts at 60° C. for several hours until the bromophenol blue tracking dye ran off the bottom of the gel. This removes unincorporated $^{32}$P-CTP.

Results: The use of the molecular clamps to reduce the overall signal from nanovariant by interfering with the replication of the undesired template was very effective with some clamp pairs. The incorporation observed from $10^9$ molecules of nanovariant replication product (row 10) was 3,557 cpm. A substantial inhibition of replication was observed in rows 3, 4, and 5. With these clamps pairs, 1&6 in row 3, 1&7 in row 4 and 2&6 in row 5 the reduction in replication, based on the incorporation of $^{32}$P-CMP, ranged from 58 to 72%. With the remaining clamp pairs little inhibition could be observed based on the total RNA made ($^{32}$P-CMP incorporated).

Inhibition of Replication by "clamps"

| | Clamps | Template | n | mean (cpm) | $\sigma_{n-1}$ (cpm) | range (cpm) |
|---|---|---|---|---|---|---|
| 1. | none | none | 8 | 608 | 781 | 8–1,886 |
| 2. | 1 & 5 | nV | 4 | 3,452 | 1,705 | 1,048–5,029 |
| 3. | 1 & 6 | nV | 4 | 1,468 | 943 | 954–2,882 |
| 4. | 1 & 7 | nV | 4 | 980 | 634 | 34–1,351 |
| 5. | 2 & 6 | nV | 4 | 1,490 | 25 | 1,459–1,515 |
| 6. | 2 & 7 | nV | 4 | 4,059 | 434 | 3,726–4,682 |
| 7. | 3 & 7 | nV | 4 | 4,056 | 314 | 3,840–4,514 |
| 8. | 4 & 5 | nV | 4 | 3,475 | 402 | 3,594–4,397 |
| 9. | 4 & 6 | nV | 4 | 3,178 | 683 | 2,479–3,836 |
| 10. | none | nV | 8 | 3,557 | 643 | 2,478–4,397 |

The average cpm for the negative controls was 608 (row 1). Three of the negatives had more than 1000 cpm incorporated.

The remaining five are under 100 cpm. Upon polyacrylamide gel electrophoresis (PAGE) analysis these three negative were identified as either nanovariant (2 cases) or MDV (1 case). These samples represent a "false positive" result. When the replication products were analyzed by 15% PAGE with 40% formamide the contaminating MDV molecules were observed in most of the samples. Based on subsequent experiments it appears that the nanovariant used to template these reactions was contaminated with MDV. The level of MDV contamination appeared to be low since the MDV replication products can only be observed when the nanovariant replication is inhibited by the antisense clamps.

Figure 2:
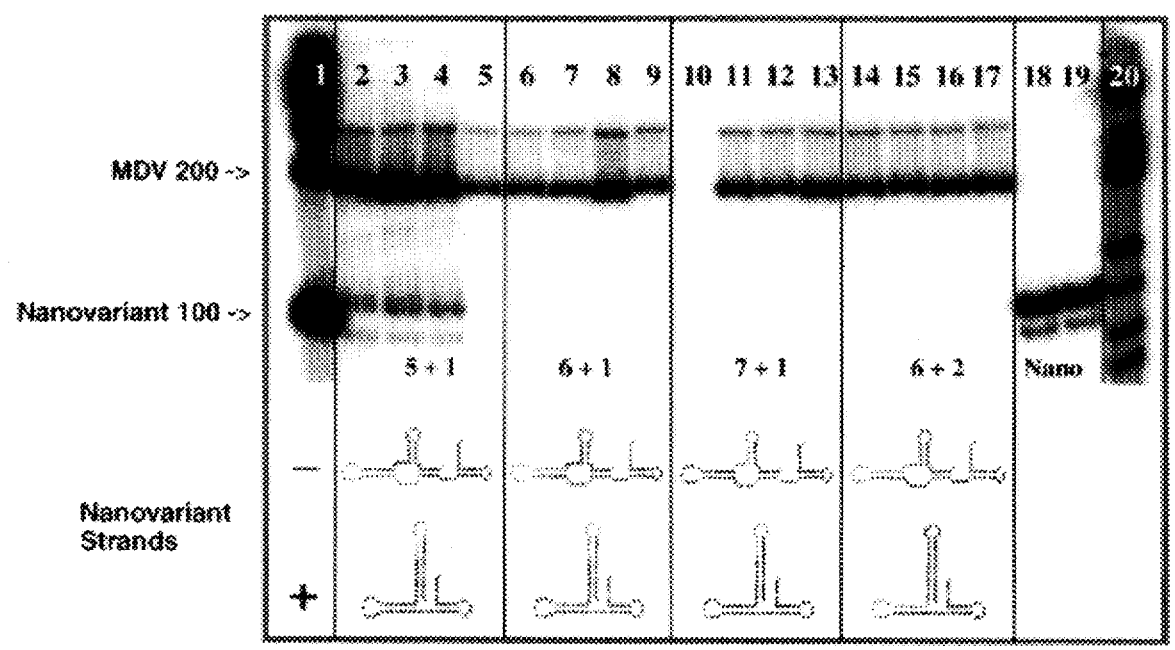
FIG. 2 displays an autoradiogram of Gel #1 from Example 3 and the depiction of the clamp binding sites of the nanovariant molecules.
Figure 3:
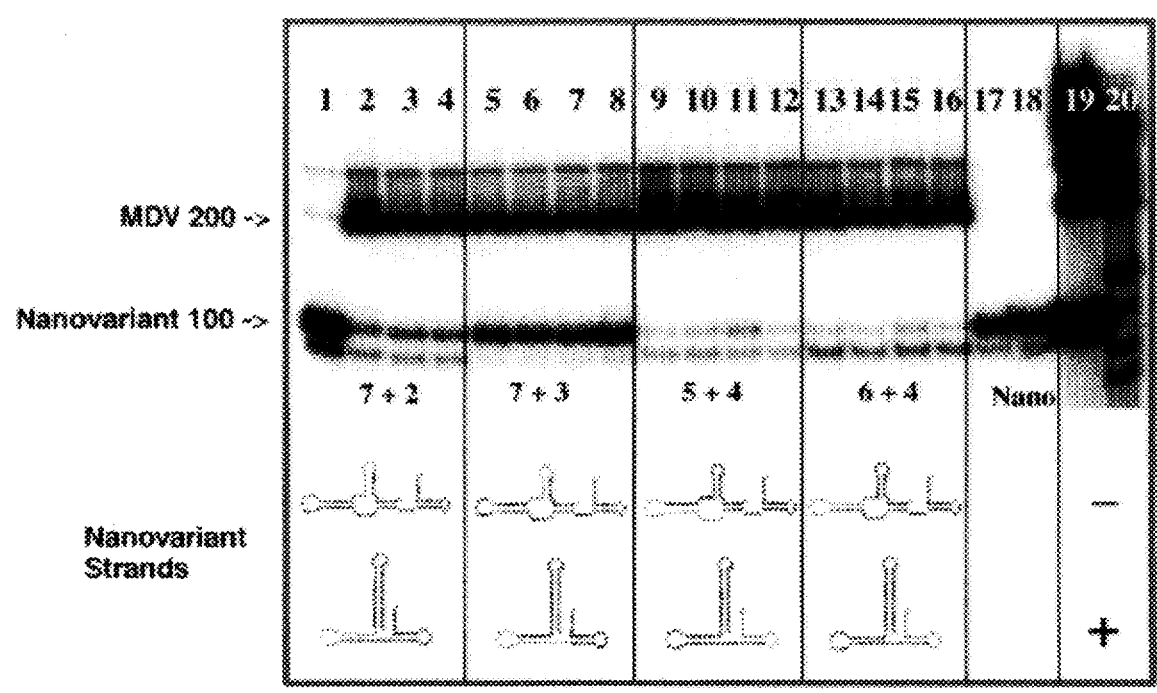
FIG. 3 displays an autoradiogram of Gel #2 from Example 3 and the depiction of the clamp binding sites of the nanovariant molecules.

Depicted in FIGS. 2 and 3 are the autoradiogram and the secondary structure models of nV with the clamp binding sites highlighted for each clamp pair used. Also shown on each gel are molecular weight markers as well as authentic nanovariant (Nano) replication product (2 lanes).

In Gel One (FIG. 2), all of the clamp pair combinations are found to inhibit nanovariant replication which MDV molecules still replicate. Several of these clamp pairs appear to be functioning very well since the nanovariant replication product cannot be detected (clamps 6&1, 7&1, 6&2). In contrast, with clamps 5&1 nanovariant replication can still be easily detected. In Gel Two, the amplification products observed with the remaining clamp pairs (7&2, 7&3, 5&4, 6&4) show some inhibition of nanovariant replication but the nanovariant replication product is still present in all cases as is the contaminating MDV. The control nanovariant when examined by PAGE migrates to the expected size for the nanovariant ~90 bases. The contaminant MDV migrates at a position consistent with its size (~220 bases).

Conclusions: The use of the molecular clamps to reduce the amplification from the nanovariant template by interfering with the replication of this undesired template was very effective with some clamp pairs. In addition with these same clamp pairs the specifity of the inhibition was evident based on the observed replication of the MDV product.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 275 bases
        ( B ) TYPE: nucleic acid
        ( C ) STRANDEDNESS: Single
        ( D ) TOPOLOGY: Linear ( i i ) MOLECULE TYPE:
        ( A ) DESCRIPTION: Called MDV-CF DNA. 55 bases of the
        human CF gene have been inserted between
        bases 61 and 62 of the MDV molecule
        (which is Sequence Number 3 in this listing)

( i i i ) HYPOTHETICAL: No ( i v ) ANTI-SENSE: No ( x i ) SEQUENCE DESCRIPTION: 1:

| | | | | | |
|---|---|---|---|---|---|
| GGGGACCCCC | CGGAAGGGGG | GACGAGGTGC | GGGCACCTCG | TACGGGAGTT | 50 |
| CGACCGTGAC | AGTATCTATA | TTCATCATAG | GAAACACCAA | AGATGATATT | 100 |
| TTCTTTAATG | GTGCCAGTCA | CGGGCTAGCG | CTTTCGCGCT | CTCCCAGGTG | 150 |
| ACGCCTCGTG | AAGAGGCGCG | ACCTTCGTGC | GTTTCGGCGA | CGCACGAGAA | 200 |
| CCGCCACGCT | GCTTCGCAGC | GTGGCCCCTT | CGCGCAGCCC | GCTGCGCGAG | 250 |
| GTGACCCCCC | GAAGGGGGGT | TCCCC | | | 275 |

( 2 ) INFORMATION FOR SEQ ID NO:2:

( i ) SEQUENCE CHARACTERISTICS:
        ( A ) LENGTH: 280 bases
        ( B ) TYPE: nucleic acid
        ( C ) STRANDEDNESS: Single
        ( D ) TOPOLOGY: Linear ( i i ) MOLECULE TYPE:
        ( A ) DESCRIPTION: Called MDV-CA DNA. Sixty bases
        complementary to the 16S rRNA gene of
        Campylobacter jejuni inserted after base 61 of
        MDV molecule (which is Sequence Number 3 in this
        listing).

( i i i ) HYPOTHETICAL: No ( i v ) ANTI-SENSE: No ( x i ) SEQUENCE DESCRIPTION: 2:

| | | | | | |
|---|---|---|---|---|---|
| GGGGACCCCC | CGGAAGGGGG | GACGAGGTGC | GGGCACCTCG | TACGGGAGTT | 50 |
| CGACCGTGAC | ACGGATTTTA | CCCCTACACC | ACCAATTCCA | TCTGCCTCTC | 100 |
| CCTCACTCTA | GACTATGAGT | TAGTCACGGG | CTAGCGCTTT | CGCGCTCTCC | 150 |
| CAGGTGACGC | CTCGTGAAGA | GGCGCGACCT | TCGTGCGTTT | CGGCGACGCA | 200 |
| CGAGAACCGC | CACGCTGCTT | CGCAGCGTGG | CCCCTTCGCG | CAGCCCGCTG | 250 |
| CGCGAGGTGA | CCCCCCGAAG | GGGGGTTCCC | | | 280 |

( 2 ) INFORMATION FOR SEQ ID NO:3:

( i ) SEQUENCE CHARACTERISTICS:
        ( A ) LENGTH: 221 bases
        ( B ) TYPE: nucleic acid
        ( C ) STRANDEDNESS: Single
        ( D ) TOPOLOGY: Linear ( i i ) MOLECULE TYPE:
        ( A ) DESCRIPTION: Called MDV DNA in this work. The
        sequence provided is the "+"strand.

( i i i ) HYPOTHETICAL: No ( i v ) ANTI-SENSE: No ( x i ) SEQUENCE DESCRIPTION: 3:

| | | | | | |
|---|---|---|---|---|---|
| GGGGACCCCC | CGGAAGGGGG | GACGAGGTGC | GGGCACCTCG | TACGGGAGTT | 50 |
| CGACCGTGAC | AAGTCACGGG | CTAGCGCTTT | CGCGCTCTCC | CAGGTGACGC | 100 |
| CTCGTGAAGA | GGCGCGACCT | TCGTGCGTTT | CGGCGACGCA | CGAGAACCGC | 150 |
| CACGCTGCTT | CGCAGCGTGG | CCCCTTCGCG | CAGCCCGCTG | CGCGAGGTGA | 200 |
| CCCCCCGAAG | GGGGGTTCCC | C | | | 221 |

( 2 ) INFORMATION FOR SEQ ID NO:4:

( i ) SEQUENCE CHARACTERISTICS:
    ( A ) LENGTH: 90 bases
    ( B ) TYPE: nucleic acid
    ( C ) STRANDEDNESS: Single
    ( D ) TOPOLOGY: Linear ( i i ) MOLECULE TYPE:
    ( A ) DESCRIPTION: Called nV DNA or Nanovariant DNA. The positive strand sequence is shown.

( i i i ) HYPOTHETICAL: No ( i v ) ANTI-SENSE: No ( x ) PUBLICATION INFORMATION:
    ( A ) AUTHORS: Schffner, W, Ruegg, K. J., and Weissmann, C.
    ( B ) TITLE: Nanovariant RNAs: nucleotide sequence and interaction with bacteriophage Q replicase.
    ( C ) JOURNAL: J. Mol. Biol.
    ( D ) VOLUME: 117
    ( E ) ISSUE:
    ( F ) PAGES: 877 to 907
    ( G ) DATE: 1977

( x i ) SEQUENCE DESCRIPTION: 4:

```
GGGGAAATCC TGTTACCAGG ATAACGGGGT TTTCTCACCT CTCTACTCGA        50
AAGTTAGAGA GGACACACCC GGATCTAGCC GGGTCAACCC                   90
```

( 2 ) INFORMATION FOR SEQ ID NO:5:

( i ) SEQUENCE CHARACTERISTICS:
        ( A ) LENGTH: 281 bases
        ( B ) TYPE: nucleic acid
        ( C ) STRANDEDNESS: Single
        ( D ) TOPOLOGY: Linear ( i i ) MOLECULE TYPE:
        ( A ) DESCRIPTION: Called MDV-CA RNA. Sixty bases complementary to the 16S rRNA gene of Campylobacter jejuni inserted after base 61 of MDV-1.

( i i i ) HYPOTHETICAL: No ( i v ) ANTI-SENSE: No ( x i ) SEQUENCE DESCRIPTION: 5:

```
GGGGACCCCC CGGAAGGGGG GACGAGGUGC GGGCACCUCG UACGGGAGUU    50
CGACCGUGAC ACGGAUUUUA CCCCUACACC ACCAAUUCCA UCUGCCUCUC   100
CCUCACUCUA GACUAUGAGU UAGUCACGGG CUAGCGCUUU CGCGCUCUCC   150
CAGGUGACGC CUCGUGAAGA GGCGCGACCU UCGUGCGUUU CGGCGACGCA   200
CGAGAACCGC CACGCUGCUU CGCAGCGUGG CCCCUUCGCG CAGCCCGCUG   250
CGCGAGGUGA CCCCCCGAAG GGGGGUUCCC C                       281
```

( 2 ) INFORMATION FOR SEQ ID NO:6:

( i ) SEQUENCE CHARACTERISTICS:
( A ) LENGTH: 20 bases
( B ) TYPE: nucleic acid
( C ) STRANDEDNESS: Single
( D ) TOPOLOGY: Linear ( i i ) MOLECULE TYPE:
( A ) DESCRIPTION: Called Nano- 44.

( i i i ) HYPOTHETICAL: No ( i v ) ANTI-SENSE: Yes ( v i i i ) POSITION IN GENOME:
   ( C ) UNITS: Base 28 to base 47 of the positive strand
      of the nanovariant sequence.

( x i ) SEQUENCE DESCRIPTION: 6:

GGTTTTCTCA CCTCTCTACT                                                                                           20

( 2 ) INFORMATION FOR SEQ ID NO:7:

( i ) SEQUENCE CHARACTERISTICS:
      ( A ) LENGTH: 17 bases
      ( B ) TYPE: nucleic acid
      ( C ) STRANDEDNESS: Single
      ( D ) TOPOLOGY: Linear ( i i ) MOLECULE TYPE:
      ( A ) DESCRIPTION: Called Nano- 64.

( i i i ) HYPOTHETICAL: No ( i v ) ANTI-SENSE: Yes ( v i i i ) POSITION IN GENOME:
      ( C ) UNITS: Base 11 to base 27 of the positive strand of
         the nanovariant sequence.

( x i ) SEQUENCE DESCRIPTION: 7:

TGTTACCAGG ATAACGG                                                                                              17

( 2 ) INFORMATION FOR SEQ ID NO:8:

( i ) SEQUENCE CHARACTERISTICS:
      ( A ) LENGTH: 90 bases
      ( B ) TYPE: nucleic acid
      ( C ) STRANDEDNESS: Single
      ( D ) TOPOLOGY: Linear ( i i ) MOLECULE TYPE:
      ( A ) DESCRIPTION: Called Nanovariant negative strand RNA
         or nanovariant "-"RNA.

( i i i ) HYPOTHETICAL: No ( i v ) ANTI-SENSE: No ( x ) PUBLICATION INFORMATION:
      ( A ) AUTHORS: Schffner, W, Ruegg, K.J., and Weissmann, C.
      ( B ) TITLE: Nanovariant RNAs: nucleotide sequence and
         interaction with bacteriophage Q replicase.
      ( C ) JOURNAL: J. Mol. Biol.
      ( D ) VOLUME: 117
      ( F ) PAGES: 877 to 907
      ( G ) DATE: 1977

( x i ) SEQUENCE DESCRIPTION: 8:

GGGUUGACCC GGCUAGAUCC GGGUGUGUCC UCUCUAACUU UCGAGUAGAG                                                           50

AGGUGAGAAA ACCCCGUUAU CCUGGUAACA GGAUUUCCCC                                                                      90

( 2 ) INFORMATION FOR SEQ ID NO:9:

( i ) SEQUENCE CHARACTERISTICS:
      ( A ) LENGTH: 90 bases
      ( B ) TYPE: nucleic acid
      ( C ) STRANDEDNESS: Single
      ( D ) TOPOLOGY: Linear ( i i ) MOLECULE TYPE:
      ( A ) DESCRIPTION: Called Nanovariant positive or "+"RNA ( i i i ) HYPOTHETICAL: No ( i v ) ANTI-SENSE: No ( x ) PUBLICATION INFORMATION:
  ( A ) AUTHORS: Schffner, W, Ruegg, K.J., and Weissmann, C.
  ( B ) TITLE: Nanovariant RNAs: nucleotide sequence and interaction with bacteriophage Q replicase.
  ( C ) JOURNAL: J. Mol. Biol.
  ( D ) VOLUME: 117
  ( F ) PAGES: 877 to 907
  ( G ) DATE: 1977

( x i ) SEQUENCE DESCRIPTION: 9:

GGGGAAAUCC UGUUACCAGG AUAACGGGGU UUUCUCACCU CUCUACUCGA                50

AAGUUAGAGA GGACACACCC GGAUCUAGCC GGGUCAACCC                           90

( 2 ) INFORMATION FOR SEQ ID NO:10:

( i ) SEQUENCE CHARACTERISTICS:
    ( A ) LENGTH: 12 bases
    ( B ) TYPE: nucleic acid
    ( C ) STRANDEDNESS: Single
    ( D ) TOPOLOGY: Linear ( i i ) MOLECULE TYPE:
    ( A ) DESCRIPTION: Called Clamp QB- 1.

( i i i ) HYPOTHETICAL: No ( i v ) ANTI-SENSE: Yes ( v i i i ) POSITION IN GENOME:
    ( C ) UNITS: Base 64 to base 75 of the negative strand nanovariant sequence.

( x i ) SEQUENCE DESCRIPTION: 10:

CCGUUAUCCU GG                                                         12

( 2 ) INFORMATION FOR SEQ ID NO:11:

( i ) SEQUENCE CHARACTERISTICS:
    ( A ) LENGTH: 18 bases
    ( B ) TYPE: nucleic acid
    ( C ) STRANDEDNESS: Single
    ( D ) TOPOLOGY: Linear ( i i ) MOLECULE TYPE:
    ( A ) DESCRIPTION: Called Clamp QB- 2

( i i i ) HYPOTHETICAL: No ( i v ) ANTI-SENSE: Yes ( v i i i ) POSITION IN GENOME:
    ( C ) UNITS: Base 37 to base 54 of the negative strand of the nanovariant sequence.

( x i ) SEQUENCE DESCRIPTION: 11:

ACUUUCGAGU AGAGAGGU                                                   18

( 2 ) INFORMATION FOR SEQ ID NO:12:

( i ) SEQUENCE CHARACTERISTICS:
    ( A ) LENGTH: 21 bases
    ( B ) TYPE: nucleic acid
    ( C ) STRANDEDNESS: Single
    ( D ) TOPOLOGY: Linear ( i i ) MOLECULE TYPE:
    ( A ) DESCRIPTION: Called Clamp QB- 3.

( i i i ) HYPOTHETICAL: No ( i v ) ANTI-SENSE: Yes (v i i i) POSITION IN GENOME:
  (C) UNITS: Base 25 to base 45 of the negative strand
       nanovariant sequence.

(x i) SEQUENCE DESCRIPTION: 12:

GUGUCCUCUC UAACUUUCGA G    21

(2) INFORMATION FOR SEQ ID NO:13:

(i) SEQUENCE CHARACTERISTICS:
    (A) LENGTH: 17 bases
    (B) TYPE: nucleic acid
    (C) STRANDEDNESS: Single
    (D) TOPOLOGY: Linear (i i) MOLECULE TYPE:
    (A) DESCRIPTION: Called Clamp QB- 4.

(i i i) HYPOTHETICAL: No (i v) ANTI-SENSE: Yes (v i i i) POSITION IN GENOME:
    (C) UNITS: Base 2 to base 18 of the negative strand
         nanovariant sequence.

(x i) SEQUENCE DESCRIPTION: 13:

GGUUGACCCG GCUAGAU    17

(2) INFORMATION FOR SEQ ID NO:14:

(i) SEQUENCE CHARACTERISTICS:
    (A) LENGTH: 23 bases
    (B) TYPE: nucleic acid
    (C) STRANDEDNESS: Single
    (D) TOPOLOGY: Linear (i i) MOLECULE TYPE:
    (A) DESCRIPTION: Called Clamp QB- 5

(i i i) HYPOTHETICAL: No (i v) ANTI-SENSE: Yes (v i i i) POSITION IN GENOME:
    (C) UNITS: Base 32 to base 54 of the positive strand
         of the nanovariant sequence.

(x i) SEQUENCE DESCRIPTION: 14:

UUCUCACCUC UCUACUCGAA AGU    23

(2) INFORMATION FOR SEQ ID NO:15:

(i) SEQUENCE CHARACTERISTICS:
    (A) LENGTH: 21 bases
    (B) TYPE: nucleic acid
    (C) STRANDEDNESS: Single
    (D) TOPOLOGY: Linear (i i) MOLECULE TYPE:
    (A) DESCRIPTION: Called Clamp QB- 6.

(i i i) HYPOTHETICAL: No (i v) ANTI-SENSE: Yes (v i i i) POSITION IN GENOME:
    (C) UNITS: Base 46 to base 66 of the positive strand
         of the nanovariant sequence.

(x i) SEQUENCE DESCRIPTION: 15:

CUCGAAAGUU AGAGAGGACA C    21

( 2 ) INFORMATION FOR SEQ ID NO:16:

( i ) SEQUENCE CHARACTERISTICS:
        ( A ) LENGTH: 16 bases
        ( B ) TYPE: nucleic acid
        ( C ) STRANDEDNESS: Single
        ( D ) TOPOLOGY: Linear ( i i ) MOLECULE TYPE:
        ( A ) DESCRIPTION: Called Clamp QB- 7.

( i i i ) HYPOTHETICAL: No ( i v ) ANTI-SENSE: Yes ( v i i i ) POSITION IN GENOME:
        ( C ) UNITS: Base 63 to base 78 of the positive strand
            of the nanovariant sequence.

( x i ) SEQUENCE DESCRIPTION: 16:

ACACACCGG AUCUAG                        1 6

We claim:

1. A process for decontaminating a mixture of nucleic acids, such mixture containing one or more desired nucleic acids and one or more contaminating nucleic acids having a known target sequence which is not present in the desired nucleic acids, comprising blocking the activity of the contaminating nucleic acids by use of antisense nucleic acids.

2. The process of claim 1 in which the decontamination occurs before amplification.

3. The process of claim 1 in which the decontamination occurs after amplification.

4. The process of claim 1 which optionally includes removal of the contaminating nucleic acids.

5. A process for identification of desired nucleic acids contained in a mixture of nucleic acids, such mixture containing one or more desired nucleic acids and one or more contaminating nucleic acids having a known target sequence which is not present in the desired nucleic acids, comprising:

a. blocking the activity of the contaminating nucleic acids by the use of antisense nucleic acids, b. amplifying from the mixture the desired nucleic acids, and c. identifying such desired nucleic acids.

6. The process of claim 5 in which the blocking comprises:

a. synthesizing a clamp to the known sequence in each contaminating nucleic acid, said clamp comprising a complementary nucleic acid, and b. adding the clamps to the mixture of nucleic acids.

7. The process of claim 6 in which the clamp has higher affinity to the target than a DNA:DNA interaction.

8. The process of claim 7 in which the clamp comprises O-2-alkyl derivatives of nucleic acid.

9. The process of claim 8 in which the clamp comprises O-2-methyl derivatives of nucleic acid.

10. The process of claim 7 in which the clamp comprises a PNA compound.

11. The process of claim 6 in which the clamp has lower affinity to the target than a DNA:DNA interaction.

12. The process of claim 6 in which the clamp has equal affinity to the target than a DNA:DNA interaction.

13. The process of claim 6 in which the clamp comprises a nucleic acid sequence to which is attached a group capable of interacting with the contaminating nucleic acid.

14. The process of claim 13 in which the interaction is due to the presence of a chemically reactive group.

15. The process of claim 14 in which the chemical interaction is a covalent bond.

16. The process of claim 5 which optionally includes removal of the contaminating nucleic acids.

17. The process of claim 5 in which the amplification scheme is based on Qβ replicase.

18. A process for identification of nucleic acids contained in a mixture of nucleic acids, such mixture containing one or more desired nucleic acids and one or more contaminating nucleic acids, comprising:

a. eliminating the contaminating nucleic acids by 1. identifying a target sequence of nucleic acids in each contaminating nucleic acid such that the target sequences do not appear in the desired nucleic acids, 2. synthesizing a clamp to each such target sequence in each contaminating nucleic acid, said clamp comprising a complementary nucleic acid, and 3. adding the clamps to the mixture of nucleic acids, b. amplifying the mixture of nucleic acids, and c. identifying such desired nucleic acids.

19. The process of claim 18 in which the clamp has higher affinity to the target than a DNA:DNA interaction.

20. The process of claim 18 in which the clamp has lower affinity to the target than a DNA:DNA interaction.

21. The process of claim 18 in which the clamp has equal affinity to the target than a DNA:DNA interaction.

22. The process of claim 18 in which the contaminating nucleic acid is from the nanovariant family, the desired nucleic acid is from the midivariant family, and the amplification system is based on Qβ replicase.

* * * * *